(12) United States Patent
Papay et al.

(10) Patent No.: US 10,004,881 B2
(45) Date of Patent: Jun. 26, 2018

(54) SYSTEM AND METHOD FOR WOUND HEALING

(71) Applicant: THE CLEVELAND CLINIC FOUNDATION, Cleveland, OH (US)

(72) Inventors: Francis A. Papay, Westlake, OH (US); Ji-Feng Chen, Lakewood, OH (US); Shengqiang Gao, Beachwood, OH (US)

(73) Assignee: THE CLEVELAND CLINIC FOUNDATION, Cleveland, OH (US)

(*) Notice: Subject to any disclaimer, the term of this patent is extended or adjusted under 35 U.S.C. 154(b) by 0 days. days.

(21) Appl. No.: 15/292,285

(22) Filed: Oct. 13, 2016

(65) Prior Publication Data

US 2017/0028175 A1 Feb. 2, 2017

Related U.S. Application Data

(60) Division of application No. 13/543,169, filed on Jul. 6, 2012, now Pat. No. 9,687,647, which is a (Continued)

(51) Int. Cl.
*A61M 27/00* (2006.01)
*A61N 1/04* (2006.01)
(Continued)

(52) U.S. Cl.
CPC ....... *A61M 27/00* (2013.01); *A61F 13/00068* (2013.01); *A61M 1/008* (2013.01);
(Continued)

(58) Field of Classification Search
CPC .. A61N 1/0428; A61N 1/0468; A61N 1/0476; A61N 1/0496; A61M 27/00; A61M 1/009; A61M 2027/004; A61M 37/00
(Continued)

(56) References Cited

U.S. PATENT DOCUMENTS 4,382,441 A * 5/1983 Svedman .......... A61F 13/00068
604/114
5,322,520 A 6/1994 Milder
(Continued)

FOREIGN PATENT DOCUMENTS

WO 2008063338 A2 5/2008
WO 2008098207 A2 8/2008
(Continued)

OTHER PUBLICATIONS

Vomaris Wound Care, Inc., "Cell Migration Enhanced with Procellera® Wireless Microcurrent Generating Wound Dressing", PR Newswire, Mar. 4, 2014, pp. 1-2.
(Continued)

*Primary Examiner* — Deanna K Hall
(74) *Attorney, Agent, or Firm* — Tarolli, Sundheim, Covell & Tummino LLP

(57) ABSTRACT

A system is provided for healing a wound. The system includes a flexible body, a therapeutic agent delivery mechanism, a suction mechanism, and a power source. The flexible body includes a cover film having oppositely disposed first and second surfaces that define a compartment. The compartment includes a first porous material, a second porous material, and at least one electrode disposed therein. The second porous material is disposed between the first porous material and the at least one electrode. The therapeutic agent delivery mechanism and the suction mechanism are fluidly connected to the compartment. The power source is in electrical communication with the at least one electrode.

9 Claims, 10 Drawing Sheets

Related U.S. Application Data continuation-in-part of application No. 12/690,786, filed on Jan. 20, 2010, now abandoned.

(60) Provisional application No. 61/505,586, filed on Jul. 8, 2011, provisional application No. 61/145,984, filed on Jan. 21, 2009.

(51) Int. Cl.
  *A61M 1/00* (2006.01)
  *A61F 13/00* (2006.01)
  *A61M 35/00* (2006.01)

(52) U.S. Cl.
  CPC ........ *A61M 1/0023* (2013.01); *A61M 1/0084* (2013.01); *A61M 1/0088* (2013.01); *A61N 1/0428* (2013.01); *A61N 1/0468* (2013.01); *A61N 1/0476* (2013.01); *A61N 1/0496* (2013.01); *A61M 35/00* (2013.01); *A61M 2205/055* (2013.01)

(58) Field of Classification Search
  USPC .................................................. 604/20, 543
  See application file for complete search history.

(56) References Cited

U.S. PATENT DOCUMENTS

| | | |
|---|---|---|
| 5,814,094 A | 9/1998 | Becker et al. |
| 5,848,998 A | 12/1998 | Marasco, Jr. |
| 5,974,344 A | 10/1999 | Shoemaker, II |
| 6,135,116 A | 10/2000 | Vogel et al. |
| 6,695,823 B1 | 2/2004 | Lina et al. |
| 6,994,702 B1 | 2/2006 | Johnson |
| 7,070,584 B2 | 7/2006 | Johnson et al. |
| 7,077,832 B2 | 7/2006 | Fleischmann |
| 7,214,202 B1 | 5/2007 | Vogel et al. |
| 7,381,859 B2 | 6/2008 | Hunt et al. |
| 7,534,240 B1 | 5/2009 | Johnson |
| 7,540,848 B2 | 6/2009 | Hannigan et al. |
| 7,553,306 B1 | 6/2009 | Hunt et al. |
| 7,569,742 B2 * | 8/2009 | Haggstrom ......... A61F 13/0203 128/888 |
| 7,611,500 B1 | 11/2009 | Lina et al. |
| 7,618,382 B2 | 11/2009 | Vogel et al. |
| 8,764,732 B2 * | 7/2014 | Hartwell ............. A61M 1/0088 604/317 |
| 2007/0179522 A1 | 8/2007 | Becker et al. |
| 2007/0239078 A1 * | 10/2007 | Jaeb ........................ A61N 7/00 601/2 |
| 2008/0262509 A1 * | 10/2008 | Clifford ................ A61M 31/00 606/109 |
| 2010/0331761 A1 | 12/2010 | Papay et al. |

FOREIGN PATENT DOCUMENTS

| | | |
|---|---|---|
| WO | 2008146224 A2 | 12/2008 |
| WO | 2010036800 A1 | 4/2010 |
| WO | 2010093753 A1 | 8/2010 |

OTHER PUBLICATIONS

PCT International Search Report and Written Opinion, dated Nov. 15, 2013, pp. 1-14.

* cited by examiner

SYSTEM AND METHOD FOR WOUND HEALING

RELATED APPLICATIONS

This application is a divisional application of U.S. patent application Ser. No. 13/543,169, filed Jul. 6, 2012, which claims the benefit of U.S. Provisional Patent Application Ser. No. 61/505,586, filed Jul. 8, 2011 and is a continuation-in-part of U.S. patent application Ser. No. 12/690,786, filed Jan. 20, 2010, which claims the benefit of U.S. Provisional Patent Application Ser. No. 61/145,984, filed Jan. 21, 2009. This application incorporates the above-identified applications herein by reference in their entirety and claims priority to all aforementioned applications for all purposes.

TECHNICAL FIELD

The present invention relates generally to a system and method for healing a wound, and more particularly to an iontophoretic, negative pressure system and method for delivering at least one therapeutic agent to a wound using a controlled, vacuum-assisted approach.

BACKGROUND OF THE INVENTION

Wounds are internal or external bodily injuries or lesions caused by physical means, such as mechanical, pressure, chemical viral, bacterial, or thermal means, which disrupt the normal continuity of structures. Such bodily injuries include contusions, wounds in which the skin is unbroken, incisions, wounds in which the skin is broken by a cutting instrument, and lacerations (e.g., wounds in which the skin is broken by a dull or blunt instrument). Wounds may also be caused by accidents or surgical procedures, in addition to pathologic conditions that cause cutaneous disruption.

When cells are injured or killed as a result of a wound, a wound healing step is desirable to resuscitate the injured cells and produce new cells to replace the dead cells. The healing process requires the reversal of cytotoxicity, the suppression of inflammation, and the stimulation of cellular viability and proliferation. Wounds require low levels of oxygen in the initial stages of healing to suppress oxidative damage, and higher levels of oxygen in the later stages of healing to promote collagen formation by fibroblasts.

One method used to promote the healing process is iontophoresis, which is a non-invasive technology for delivering nutrients, medicines, vitamins, minerals, therapeutic agents, drugs, or other bioactive agents using a small electric current, which causes an electrical field. In general, delivering such medicaments through iontophoresis involves applying an electromotive force that transports ions through the stratum corneum, the outermost layer of skin, and into the dermis, the inner layer of skin comprised of connective tissue, blood and lymph vessels, sweat glands, hair follicles, and an elaborate sensory nerve network. This same electromotive force can also transport ions through other subcutaneous tissue planes, would granulation tissues, and biofilms.

Certain drawbacks exist for using iontophoresis to treat dermatological wounds, however. For example, treating wounds (e.g., dermatological wounds) using iontophoresis can cause localized pH alterations as a result of accumulation of electrolysis products and cellular necrosis. The build-up of such products can then shield bacteria, fungi, etc. in the region from penetration of therapeutic agents to the proper tissue depth.

SUMMARY OF THE INVENTION

According to one aspect of the present invention, a system is provided for healing a wound of a subject. The system comprises a flexible body, a therapeutic agent delivery mechanism, a suction mechanism, and a power source. The flexible body includes a cover film having oppositely disposed first and second surfaces that define a compartment. The compartment includes a first porous material, a second porous material, and at least one electrode disposed therein. The second porous material is disposed between the first porous material and the at least one electrode. The therapeutic agent delivery mechanism and the suction mechanism are in fluid communication with the compartment. The power source is in electrical communication with the at least one electrode.

According to another aspect of the present invention, a method is provided for healing a wound. One step of the method includes providing a system comprising a flexible body, a therapeutic agent delivery mechanism, a suction mechanism, and a power source. The flexible body includes a cover film having oppositely disposed first and second surfaces that define a compartment. The compartment includes a first porous material, a second porous material, and at least one electrode disposed therein. The second porous material is disposed between the first porous material and the at least one electrode. The therapeutic agent delivery mechanism and the suction mechanism are in fluid communication with the compartment. The power source is in electrical communication with the at least one electrode. Next, a wound-contacting portion of the compartment is placed into contact with the wound. At least one therapeutic agent is then delivered to the wound, followed by activation of the suction mechanism to remove at least one of fluid or debris from the wound. The method is optionally repeated until the wound is sufficiently healed.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1A:
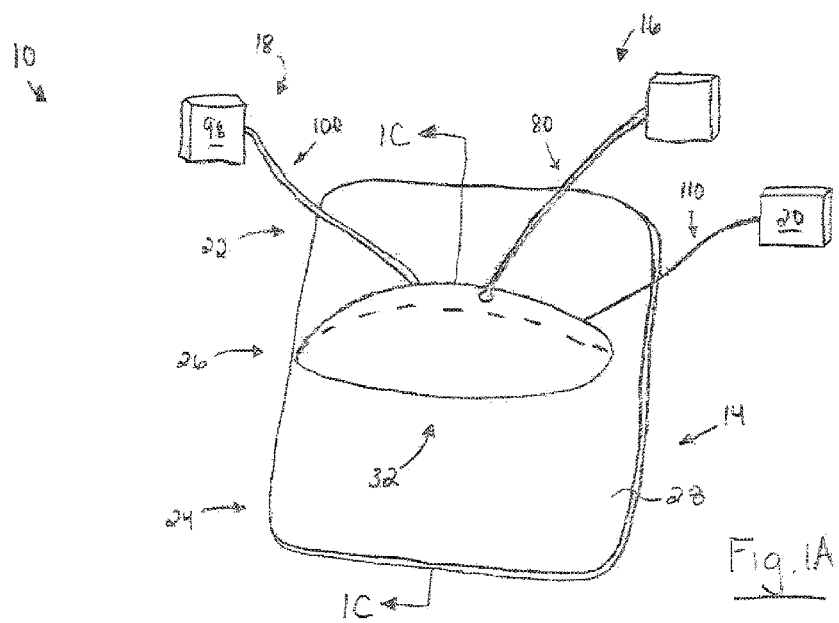
FIG. 1A is a perspective view showing a system for healing a wound constructed in accordance with one aspect of the present invention.

Unless otherwise defined, all technical terms used herein have the same meaning as commonly understood by one of ordinary skill in the art to which the present invention pertains.

As used in the context of the present invention, the term "subject" can refer to any warm-blood organism including, but not limited to, human beings, pigs, rats, mice, dogs, goats, sheep, horses, monkeys, apes, rabbits, cattle, etc.

As used herein, the terms "therapeutic agent", "drug", "agent", "chemical compound", and "chemical substance" can refer to any therapeutically effective molecule or moiety (i.e., molecules or moieties that are capable of having a biological effect), such as pharmaceutical agents, drugs, or biological agents.

As used herein, the term "wound" can refer to damage or loss to any one or combination of skin layers caused by cuts, incisions (including surgical incisions), abrasions, microbial infections, diseases or disorders, necrotic lesions, lacerations, fractures, contusions, burns and amputations. Non-limiting examples of wounds can include bed sores, thin dermis, bullous skin disease, and other cutaneous pathologies, such as subcutaneous exposed wounds that extend below the skin into the subcutaneous tissue. In some instances, a subcutaneous exposed wound may not affect underlying bones or organs.

As used herein, the terms "treatment" and "treating" can refer to obtaining a desired physiologic, dermatological, or cosmetic effect by the present invention. The effect may be prophylactic in terms of completely or partially preventing a disease, disorder, or symptom thereof and/or may be therapeutic in terms of a partial or complete cure for a disease, disorder, and/or symptom attributable to the disease or disorder. Thus, the terms can cover any treatment of a disorder or disease in a subject, such as: (a) preventing a wound from occurring in a subject that may be predisposed to developing the wound but has not yet been diagnosed as having it; (b) inhibiting a wound, e.g., arresting its development; and (c) relieving, alleviating, or ameliorating a wound by, for example, causing regression of the wound.

As used herein, the term "cosmetic effect" can refer to any treatment by the present invention that preserves, restores, bestows, simulates, or enhances the appearance of bodily beauty or appears to enhance the beauty or youthfulness, specifically as it relates to the appearance of tissue or skin.

As used herein, the terms "healing" and "heal" can refer to improving the natural cellular processes and humoral substances of tissue repair such that healing is faster, and/or the resulting healed area has less scaring, and/or the wounded area possesses tissue strength that is closer to that of uninjured tissue, and/or the wounded tissue attains some degree of functional recovery. The terms can additionally or alternatively refer to the physiological process wherein a wounded area returns to an effectively normal state. When the wound is an open wound, for example, healing can refer to the process whereby the skin or mucosa re-forms a continuous barrier. The skilled artisan will appreciate that, after healing, the area of the wound may comprise scar tissue that is not identical to the surrounding tissue.

As used herein, the term "operably connected" can refer to a connection between components or entities whereby the one entity is in some way attached to a second entity. An operable connection can be directly between first and the second entities, for example, through the use of threaded fasteners, plastic or metallic tube fittings, nails, chemical adhesives, tape, weldment, or the like. A direct connection between first and the second entities can be non-detachable, for example, through the use of chemical adhesives or weldment, or detachable, for example, through the use of removable fasteners, such as threaded fasteners. Alternatively, an operable connection can be indirectly between first and the second entities via one or more intermediate entities.

As used herein, the term "fluid communication" can refer to two chambers, vessels, tanks, or other structures containing a fluid, such as a liquid or gas, where the fluid-containing structures are connected together (e.g., by a line, pipe or tubing) so that a fluid can flow between the two fluid-containing structures. Therefore, two chambers that are in "fluid communication" can, for example, be connected together by a line between the two chambers, such that a fluid can flow freely between the two chambers.

As used herein, the term "electrical communication" can refer to the ability of a generated electric field to be transferred to, or have an effect on, one or more components of the present invention. In some instances, the generated electric field can be directly transferred to a component (e.g., via a wire or lead). In other instances, the generated electric field can be wirelessly transferred to a component.

Figure 1B:
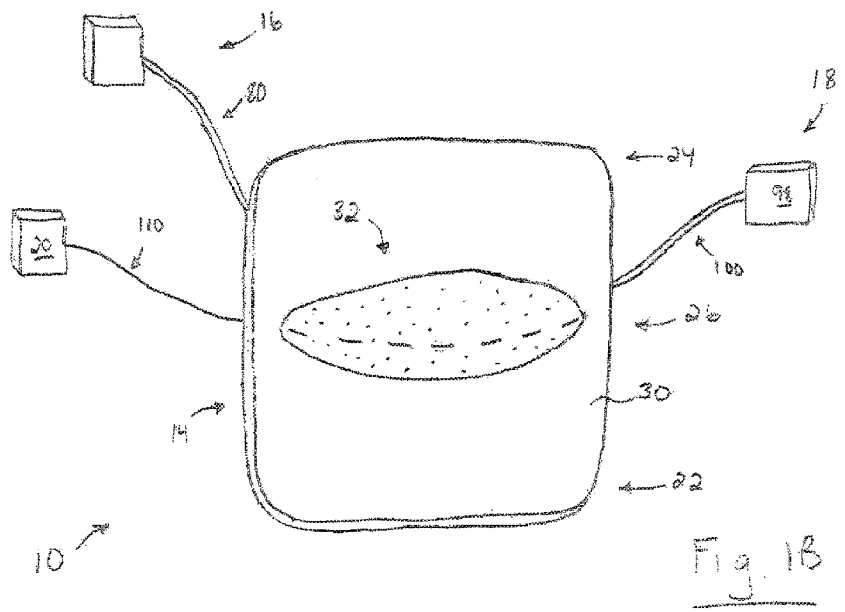
FIG. 1B is an alternative perspective view of the system in FIG. 1A.
Figure 1C:
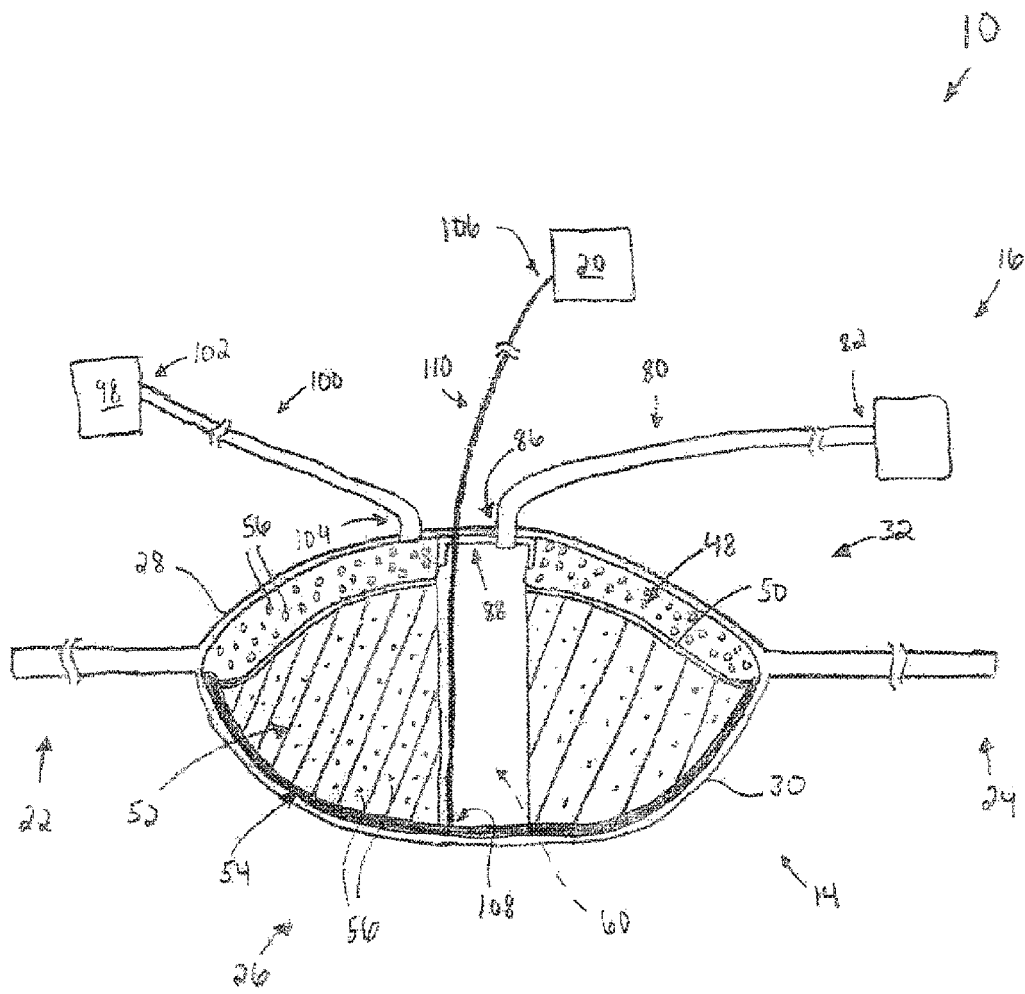
FIG. 1C is a cross-sectional view taken along Line 1C-1C in FIG. 1A.
Figure 7:
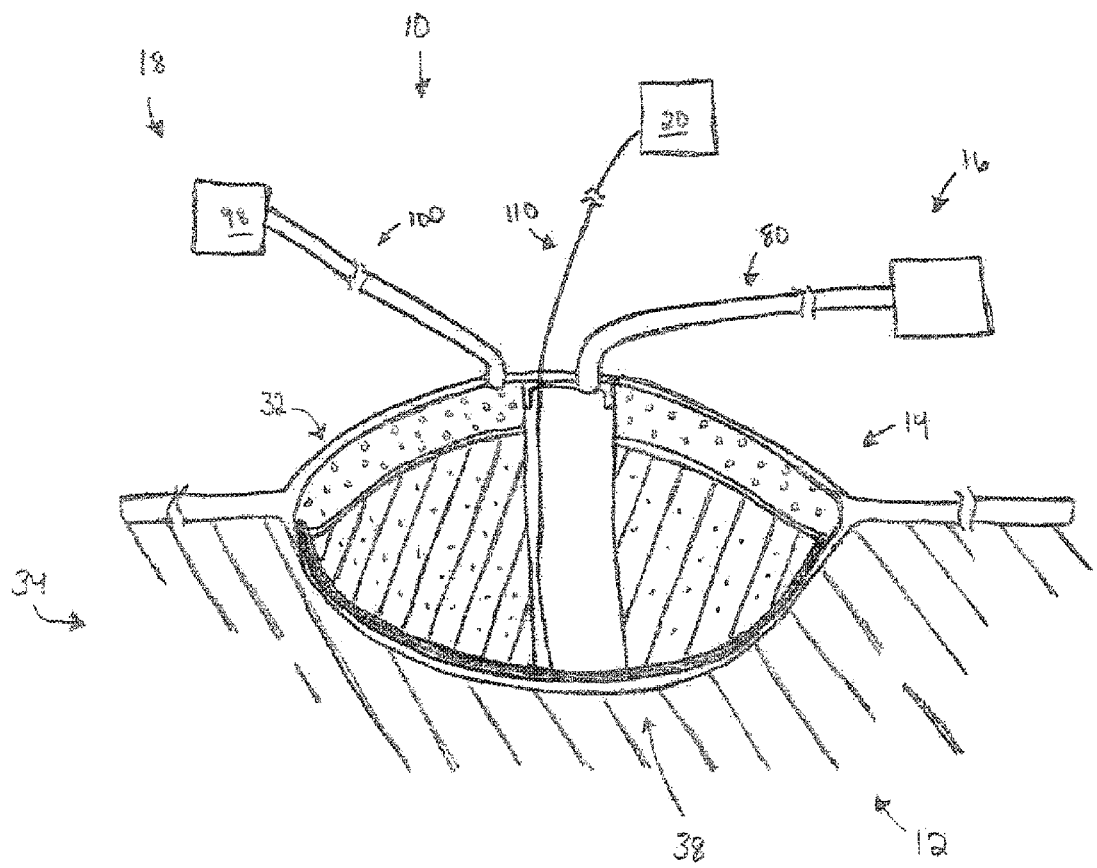
FIG. 7 is a cross-sectional view showing the system of FIGS. 1A-C placed in contact with a wound.

The present invention relates generally to a system and method for healing a wound (e.g., a dermatological or subcutaneous exposed wound), and more particularly to an iontophoretic, negative-pressure system and method for delivering at least one therapeutic agent to a wound using a controlled, vacuum-assisted approach. As representative of one aspect of the present invention, FIGS. 1A-C illustrate a system 10 for healing a wound 12 (FIG. 7). The present invention can be used to seamlessly control drug flow patterns in and about a wound 12 while also removing unwanted materials from the wound site, such as bacteria and other debris. In doing so, the present invention maximizes tissue perfusion and the interaction between therapeutic agents and wound tissue. Although the present invention is described below in terms of treating decubital ulcers or "bed sores", it will be appreciated that any other type of wound 12 can be treated by the present invention.

One aspect of the present invention includes a system 10 for healing a wound 12 in a subject. As shown in FIGS. 1A-C, the system 10 generally comprises a flexible body 14, a therapeutic agent delivery mechanism 16, a suction mechanism 18, and a power source 20. The flexible body 14 has a substantially rectangular shape; however, it will be appreciated that the shape and dimensions (e.g., length, width, thickness) of the flexible body can be varied (e.g., oval-shaped, square-shaped, etc.) depending upon the particular application of the system 10 (e.g., the dimensions of the wound 12). The flexible body 14 includes oppositely disposed first and second end portions 22 and 24 and a middle portion 26 extending between the first and second end portions. The flexible body 14 comprises a cover film having oppositely disposed first and second surfaces 28 and 30 that define a compartment 32, which is generally located at the middle portion 26. As shown in FIGS. 1A-C, each of the first and second end portions 22 and 24 of flexible body 14 has a flattened or planar configuration and is adapted for flush placement against the skin 34 (FIG. 7) of a subject. All or only a portion of the flexible body 14 (FIGS. 1A-C) can be made from a medical-grade, biocompatible polymeric material, such as silicon, polyethylene and poly(methyl methacrylate).

The compartment 32 defined by the first and second surfaces 28 and 30 has an egg-shaped or bulbous configuration; however, it will be appreciated that other shapes and configurations are possible. Although the compartment 32 is shown as being generally located at the middle portion 26 of the flexible body 14, it will be appreciated that the location of the compartment, as well as the portion of the flexible body comprising the compartment, can be varied as needed.

Figure 2A:
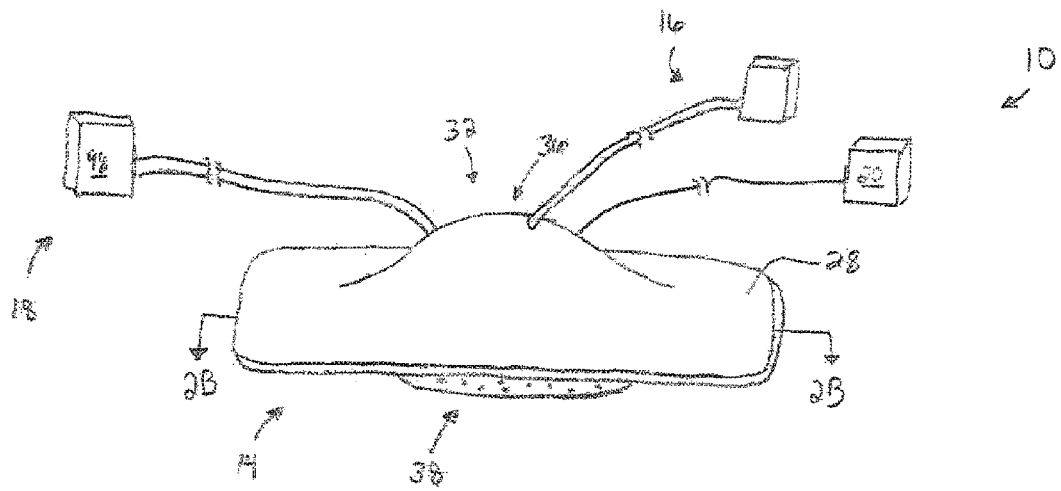
FIG. 2A is a perspective view taken from one side of the system in FIGS. 1A-C.
Figure 2B:
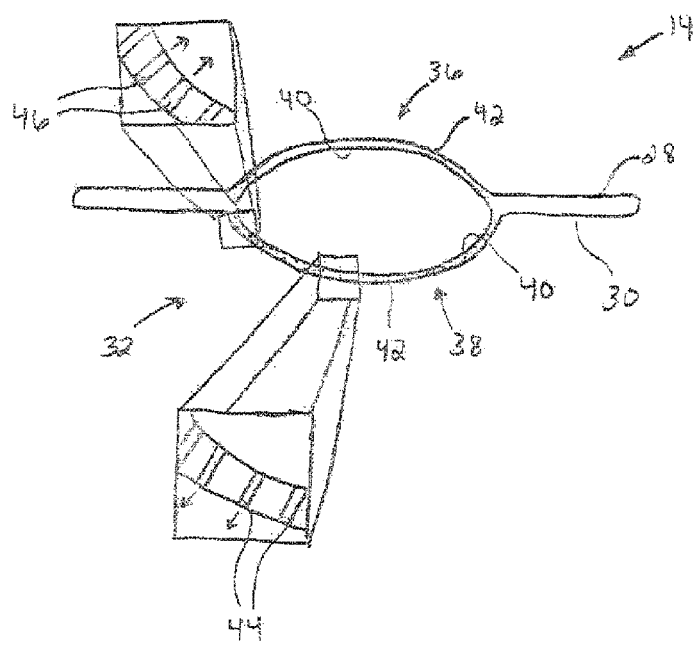
FIG. 2B is a cross-sectional view taken along Line 2B-2B in FIG. 2A.

As shown in FIGS. 2A-B, the compartment 32 comprises an upper portion 36 and a lower wound-contacting portion 38, each of which is defined by an inner wall 40 and an outer wall 42. At least a portion of the wound-contacting portion 38 is porous and includes a series of output ports 44 and uptake ports 46 that extend between the inner and outer walls 40 and 42. The dimensions (e.g., diameter, length, etc.) of the output and uptake ports 44 and 46 can be varied as needed so that the wound-contacting portion 38 can function, where desired, as a rate-controlling membrane. As described in more detail below, the output and uptake ports 44 and 46 respectively facilitate movement of a solution containing at least one therapeutic agent and debris and/or fluid throughout the compartment 32 and the wound 12.

Figure 3A:
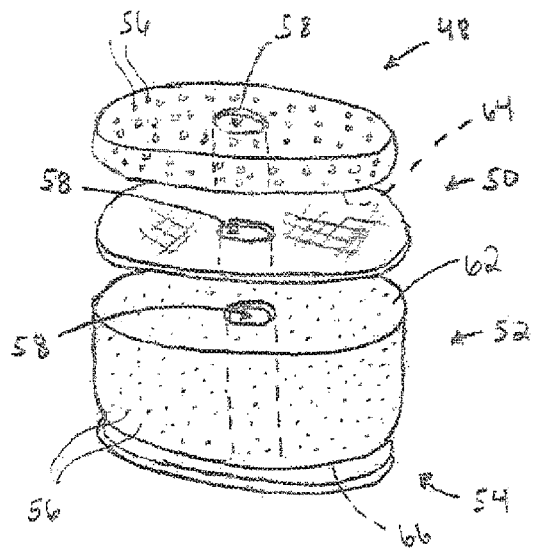
FIG. 3A is an exploded perspective view showing a first porous material, a sheet member, a second porous member, and an electrode comprising the system in FIGS. 1A-C.
Figure 3B:
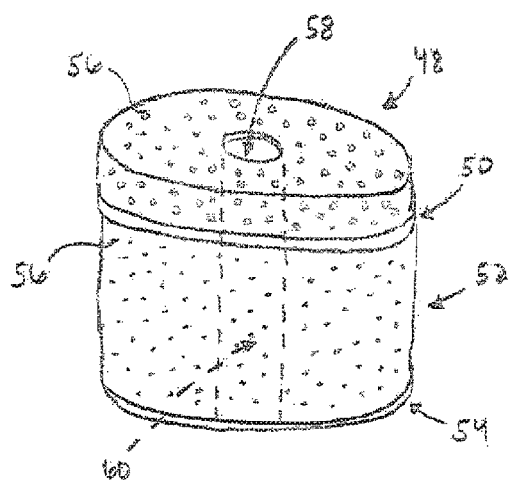
FIG. 3B is an assembled perspective view of the first porous material, the sheet member, the second porous member, and the electrode in FIG. 3A.

The compartment 32 includes a first porous material 48 (FIGS. 3A-B), a sheet member 50, a second porous material 52, and at least one electrode 54 that are snugly disposed therein. As shown in FIGS. 3A-B, each of the first and second porous materials 48 and 52 has a substantially toroidal shape and includes a plurality of pores 56 extending therethrough. The first and second porous materials 48 and 52 generally comprise a matrix formed from a sponge or gel (e.g., a hydro-gel). The dimensions of the pores 56 comprising the first porous material 48 can be the less than, the same as, or greater than the dimensions of the pores comprising the second porous material 52. Each of the first and second porous materials 48 and 52, as well as the sheet member 50 includes a central opening 58 that collectively form a channel 60. It will be appreciated that the shape and dimensions (e.g., length, height, thickness) of the first and second porous materials 48 and 52, as well as the sheet member 50 can be varied to ensure a snug fit within the compartment 32.

The material(s) used to form the first and second porous materials 48 and 52 can include any one or combination of materials that permit the flow of a fluid and/or debris from a wound 12 therethrough. For example, the first porous material 48 and/or the second porous material 52 can be comprised of a biocompatible, non-biodegradable polymeric material made from a homopolymer, a copolymer, straight polymers, branched polymers, cross-linked polymers, stimuli-responsive polymers, or a combination thereof. Examples of such polymers can include silicone, polyvinyl alcohol, ethylene vinyl acetate, polylactic acid, nylon, polypropylene, polycarbonate, cellulose, cellulose acetate, polyglycolic acid, polylactic-glycolic acid, cellulose esters, polyethersulfone, acrylics, their derivatives, and combinations thereof.

The sheet member 50 is disposed between the first and second porous materials 48 and 52 and functions as a partition to substantially prevent the movement of fluid between the first and second porous materials. The sheet member 50 is dimensioned so that the sheet member extends across substantially the entire upper and lower surfaces 62 and 64 of the second and first porous materials 52 and 48, respectively. The sheet member 50 can be made of a substantially impermeable material, such as a medical-grade polymeric material (e.g., silicon). Compared to the first and second porous materials 48 and 52, the thickness of the sheet member 50 can be relatively thin. For example, the sheet member 50 can have a thin film configuration. In another example, the thickness of the sheet member 50 can be less than the thickness of each of the first and second porous materials 48 and 52.

As shown in FIGS. 3A-B, at least one electrode 54 is disposed about a lower surface 66 of the second porous material 52. The at least one electrode 54 can comprise any one or combination of electrodes capable of providing an electric field sufficient to motivate at least one therapeutic agent into a wound 12 and/or tissue surrounding the wound. To ensure proper transmission of electrical energy, the at least one electrode 54 includes at least two separate, electrically-conductive portions or components (not shown in detail) that are biased against one another. The at least one electrode 54 can be made from one or a combination of flexible, electrically-conductive materials that are capable of conducting an electric current. For example, materials used to form the at least one electrode 54 can include metals or metal alloys, such as platinum, platinum-iridium, stainless steel, gold, copper, gold-plated copper, zinc or the like. Additionally or optionally, at least a portion of the at least one electrode 54 can be embedded within a polymeric material (or other similar material) (e.g., silicone) to protect wound tissue from abrasion and promote biocompatibility and/or electrical conduction.

The at least one electrode 54 can comprise any regularly-shaped, irregularly-shaped, uniform, and/or non-uniform electrode capable of providing a uniform or non-uniform electric field sufficient to motivate any polarizable chemical compound, including compounds that are difficult to polarize, such as non-polar drugs and large molecule compositions into a wound 12 and/or tissue surrounding a wound. In one example of the present invention, the at least one electrode 54 can comprise a first electrically-conductive material (e.g., a treatment electrode) (not shown) and a second electrically-conductive material (e.g., a return electrode) (not shown) that are adapted for motivating, or causing the migration of, ionizable therapeutic molecules via iontophoresis. In another example of the present invention, the at least one electrode 54 can comprise an interdigitated electrode (not shown) capable of providing a non-uniform electric field to an area sufficient to induce dielectrophoretic transport of at least one therapeutic agent.

Figure 4A:
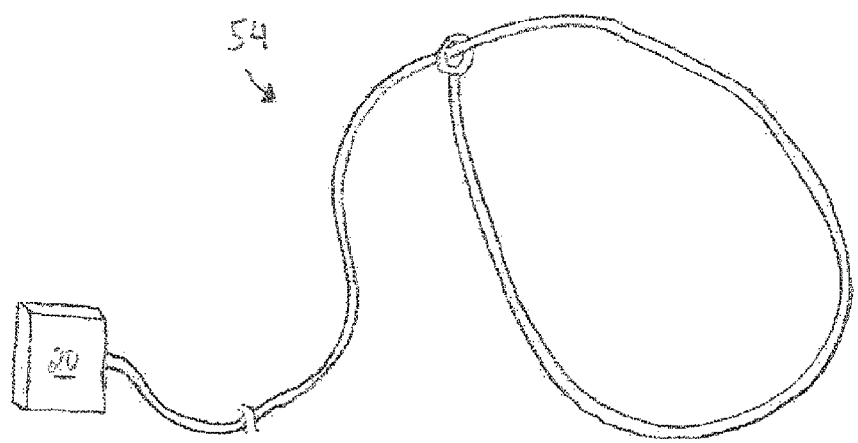
FIG. 4A is a perspective view showing one configuration of the electrode in FIGS. 3A-B.

In one example of the present invention, the at least one electrode 54 can comprise a lasso-shaped electrode as shown in FIG. 4A.

Figure 4B:
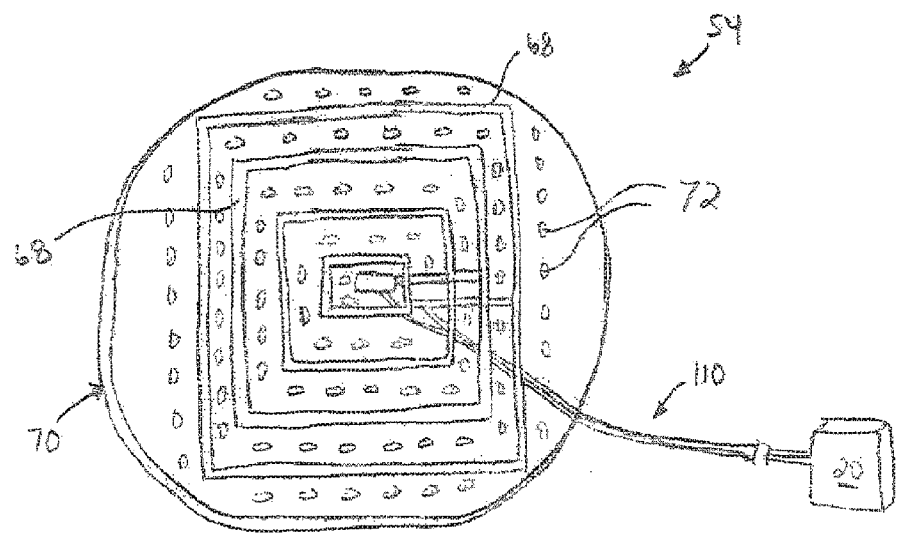
FIG. 4B is a perspective view showing another configuration of the electrode in FIGS. 3A-B.

In another example of the present invention, the at least one electrode 54 can comprise two or more independent, electrically-conductive members 68 (FIG. 4B) separated by an insulator 70, which includes a series of pores 72 extending therethrough.

Referring again to FIGS. 1A-C, the system 10 additionally includes a therapeutic agent delivery mechanism 16 that is in fluid communication with the compartment 32. The therapeutic agent delivery mechanism 16 generally comprises a valve 74 (FIG. 5), a therapeutic agent source 76 that is in fluid communication with the valve, and an oxygen source 78 that is also in fluid communication with the valve.

The therapeutic agent delivery mechanism 16 is fluidly connected to the compartment 32 by a first fluid line 80, such as medical-grade tubing. For example, a first end 82 of the first fluid line 80 is securely connected to a fluid output portion 84 of the valve 74, while a second end 86 of the first fluid line is securely connected to the compartment 32. As shown in FIG. 1C, the second end 86 of the first fluid line 80 is securely connected to the compartment 32 via a cap member 88. The cap member 88 can be comprised of a polymeric material and be affixed (e.g., glued, stapled, stitched, etc.) to the upper portion 36 of the compartment 32. The second end 86 of the first fluid line 80 extends through the inner and outer walls 40 and 42 of the upper portion 36 of the compartment 32, through the cap member 88, and into communication with the channel 60.

Figure 5:
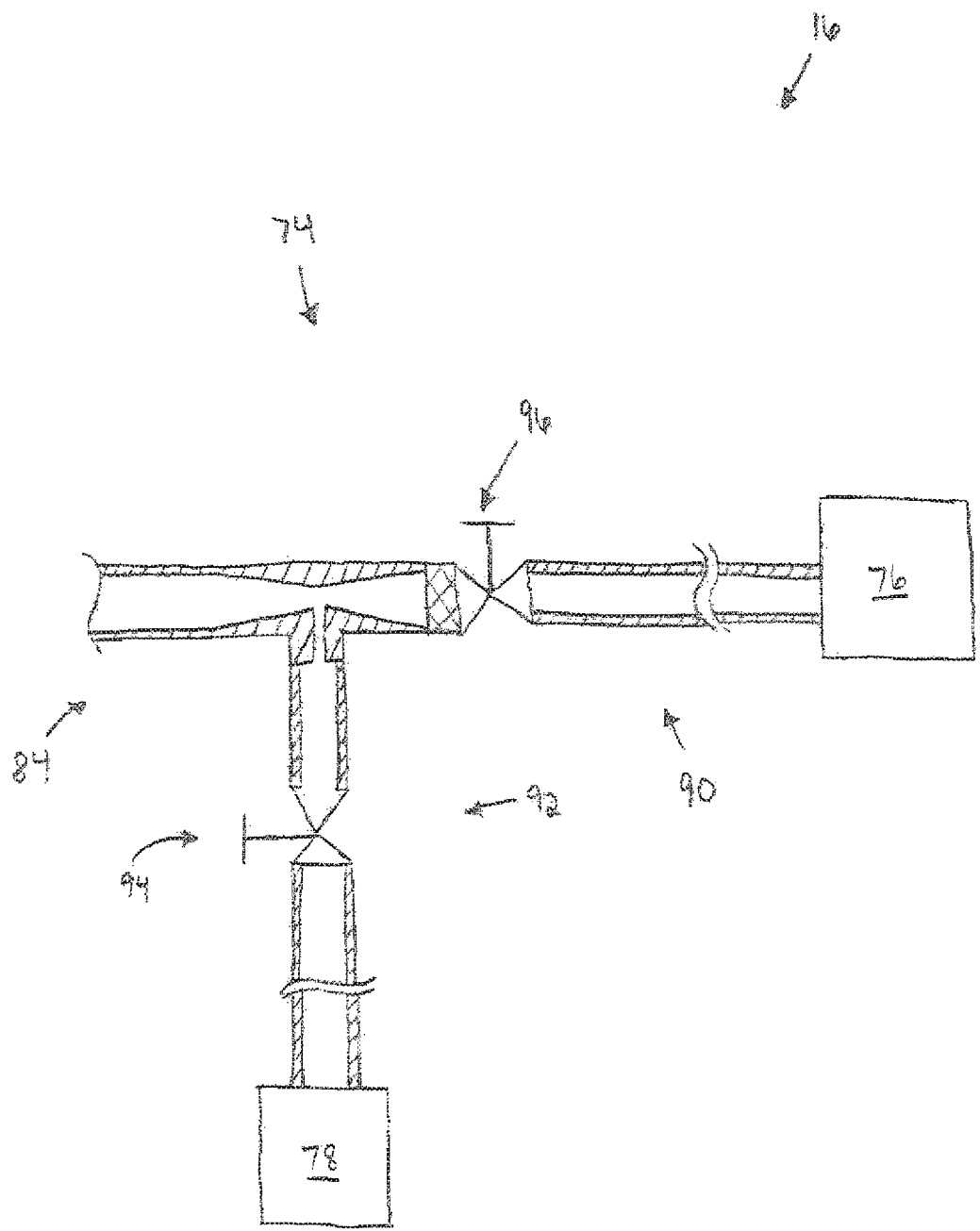
FIG. 5 is a cross-sectional view of a Venturi valve constructed in accordance with one aspect of the present invention.

The valve 74 comprising the therapeutic agent delivery mechanism 16 can include any valve that is capable of controllably mixing oxygen with a solution containing one or more therapeutic agents. In one example of the present invention, the valve 74 can comprise a Venturi valve as shown in FIG. 5. The Venturi valve has a T-shaped configuration and includes a fluid output portion 84, a fluid input portion 90, and an oxygen input portion 92. As noted above, the fluid output portion 84 is in fluid communication with the first end 82 of the first fluid line 80. Additionally, the fluid input portion 90 and the oxygen input portion 92 are in fluid communication with the therapeutic agent source 76 and the oxygen source 78, respectively, by separate fluid lines (not shown). The Venturi valve also includes first and second check valves 94 and 96 for adjusting the flow of oxygen and the solution containing one or more therapeutic agents, respectively, through the Venturi valve.

The therapeutic agent source 76 can include any container or vessel capable of retaining and dispensing a volume of the solution containing one or more therapeutic agents. Non-limiting examples of suitable containers or vessels can include syringes, bottles, tanks, and vats that are optionally connected to a pump (not shown). The therapeutic agent(s) comprising the solution are selected based upon the particular type (or types) of wound(s) being treated. Examples of therapeutic agents can include dermatological agents, antibacterial agents, antifungal agents, anticonvulsant agents, antihypertensive agents, anticancer agents, immunomodulatory agents, antiviral agents, anesthetics, analgesics, tranquilizers, sedatives, muscle relaxants, non-steroidal anti-inflammatory agents, cosmetic agents, biologics, small molecules, polynucleotides, polypeptides and steroids. Other examples of therapeutic agents, such as those that can be used for cosmetic or aesthetic purposes can include botox, botulinum toxin, hyaluronic acid, collagen and elastin.

More specific examples of therapeutic agents can include vitamin A, C, D or E, alpha-hydroxy acids, such as pyruvic, lactic or glycolic acids, beta-hydroxy acids, caffeine, theobromine, lanolin, vaseline, aloe vera, methyl or propyl parban, pigments, dyes and the like for tattooing and make-up effects, estrogen, make-up agents, anti-aging agents, pigments, such as iron oxide and titanium oxide for use after dermabrading for tattoo removal, iodine to reduce scar tissue, nutrients, DNA, RNA, corticosteroids and -caine-type compounds, such as lidocaine in base form, estradiol, progesterone, demegestone, promegestone, testosterone and their esters, nitro-compounds, such as nitroglycerine and isosorbide nitrates, nicotine, chlorpheniramine, terfenadine, triprolidine, hydrocortisone, oxicam derivatives, such as piroxicam, ketoprofen, mucopolysaccharides, such as thiomucase, buprenorphine, fentanyl and its analogs, naloxone, codeine, dihydroergotamine, pizotiline, salbutamol, terbutaline, prostaglandins, such as misprostol and emprostil, omeprazole, imipramine, benzamides, such as metaclopramide, scopolamine, peptides, such as growth releasing factor, epidermal growth factor and somatostatin, cloidine, dihydroxypyridines, such as nifedipine, verapamil, ephedrine, proanolol, metoprolol, spironolactone, thiazides, such as hydrochlorothiazide, flunarizine, syndone imines, such as molsiodmine, sulfated polysaccharides, such as heparin fractions, and salts of such compounds with physiologically acceptable acids and bases.

The oxygen source 78 comprising the therapeutic agent delivery mechanism 16 can include any suitable oxygen reservoir, such as a pressurized tank. The oxygen source 78 can hold 100% pure oxygen or, alternatively, any lesser concentration of oxygen, such as air (e.g., about 20% oxygen).

As shown in FIGS. 1A-C, the system 10 additionally includes a suction mechanism 18 that is in fluid communication with the compartment 32. The suction mechanism 18 can comprise a vacuum source 98 that is in fluid communication with the compartment 32 via a second fluid line 100 (e.g., medical-grade tubing). For example, a first end 102 of the second fluid line 100 is securely connected to the vacuum source 98, while a second end 104 of the second fluid line is securely connected to the compartment 32. As shown in FIG. 1C, the second end 104 of the second fluid line 100 extends through the upper portion 36 of the compartment 32 so that the lumen of the second fluid line is in fluid communication with the first porous material 48. The second end 104 of the second fluid line 100 can be affixed to the compartment 32 via any known method, such as gluing, stapling, stitching, etc. The vacuum source 98 can include any device or apparatus capable of generating or providing negative pressure within a portion of the compartment 32. For example, the vacuum source 98 can comprise a pump (not shown). The suction mechanism 18 can be operated at or below atmospheric pressure (i.e., negative pressure), and can be applied constantly, periodically, or cyclically. As described in more detail below, the suction mechanism 18 can promote wound healing by removing fluid and/or debris that accumulates at or within the wound 12.

The system 10 also includes a power source 20 that is in electrical communication with the at least one electrode 54 and capable of delivering an electrical signal to the at least one electrode. The power source 20 is capable of providing an AC signal, a DC signal, or a combination thereof. In some instances, the power source 20 is configured to provide a signal having certain characteristics. As described below, the certain characteristics can include at least one orienting frequency and at least one motivating frequency. The power source 20 can be electrically connected to the at least one electrode 54 via a direct electrical link or a wireless link (e.g., an RF link). As shown in FIGS. 1A-C, for example, proximal and distal ends 106 and 108 of an electrical lead 110 can be electrically connected to the power source 20 and the at least one electrode 54, respectively.

Figure 6:
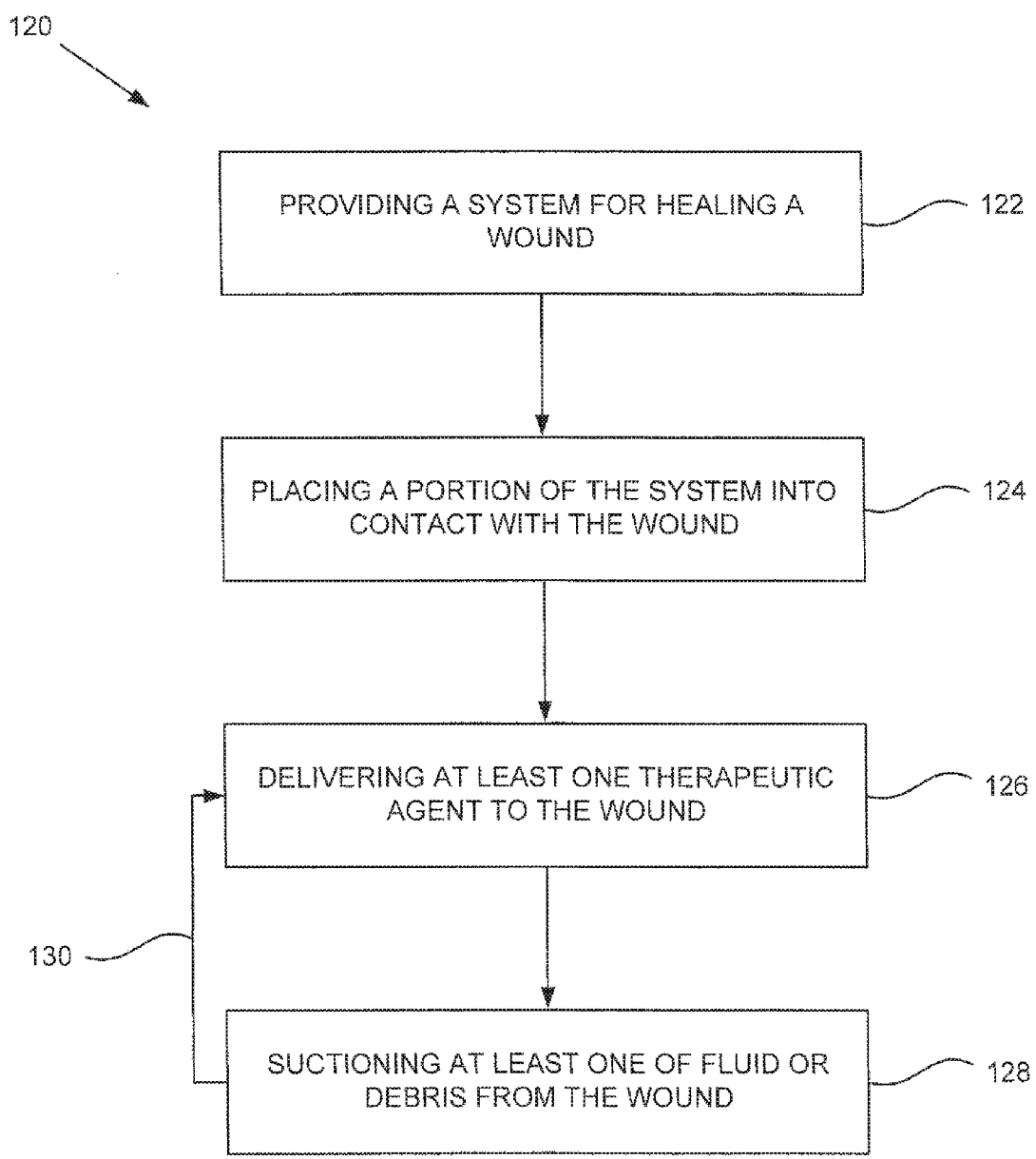
FIG. 6 is a process flow diagram illustrating a method for healing a wound according to another aspect of the present invention.

FIG. 6 is a process flow diagram illustrating another aspect of the present invention. In FIG. 6, a method 120 is provided for healing a wound 12. At Step 122, the method 120 includes providing a system 10 for healing a wound 12. The system 10 can be identically or similarly configured as the system shown in FIGS. 1A-C. For example, the system 10 can comprise a flexible body 14, a therapeutic agent delivery mechanism 16, a suction mechanism 18, and a power source 20. It will be appreciated that other medical instruments or apparatus can be used to supplement one or more steps of the method 120, depending upon the particular type of wound 12 being treated.

At Step 124, a portion of the system 10 is placed into contact the wound 12. The particular placement location, type of therapeutic agent (or agents), and the size and shape of the flexible body 14 will depend upon the type of wound 12 being treated (e.g., deep or shallow, acute or non-acute, etc.), the location of the wound, the subject's age, any underlying disease(s) or condition(s), as well as other factors. For example, application of the system 10 to the wound 12 can be done as soon as possible following an acute injury. Depending upon the type of injury, however, application of the system 10 to the wound 12 may be initiated any time after injury or whenever deemed medically necessary. Before placement of the system 10 at Step 124, cleaning and debridement of the wound 12 may be needed.

As shown in FIG. 7, the wound-contacting portion 38 of the compartment 32 is placed into contact with the wound 12 so that the wound-contacting portion partially or completely covers the wound. Where the subject is suffering from a bed sore, for example, the entire surface of the bed sore can be covered by the wound-contacting portion 38. When applying the wound-contacting portion 38 to the wound 12, care should be taken to eliminate or reduce the presence of void spaces between the outer wall 42 of the wound-contacting portion 38 and the wound, which can result in inadequate treatment at those points.

If it has not been done so already, the suction mechanism 18, the power source 20, and the therapeutic agent delivery mechanism 16 can be operably connected with the flexible body 14 (as discussed above). After doing so, the therapeutic agent delivery mechanism 16 is activated so that a volume of the solution containing the therapeutic agent (or agents) is delivered to the wound 12 at a desired rate and frequency (e.g., continuously, periodically, etc.) (Step 126). As described above, the solution containing the therapeutic agent(s) is simultaneously flowed through the valve 74 (e.g., Venturi valve) along with oxygen. Using the first check valve 94, the amount of oxygen mixed with the solution can be varied as needed. The oxygen content in the solution can be selectively increased by increasing the flow of oxygen into the valve 74. Since oxygen is crucial for wound healing, delivery of more oxygen into the wound 12 advantageously promotes wound healing. As the solution containing the therapeutic agent(s) is flowed through the first fluid line 80, the solution is delivered into the channel 60 and thereby saturates the second porous material 52.

Figure 8:
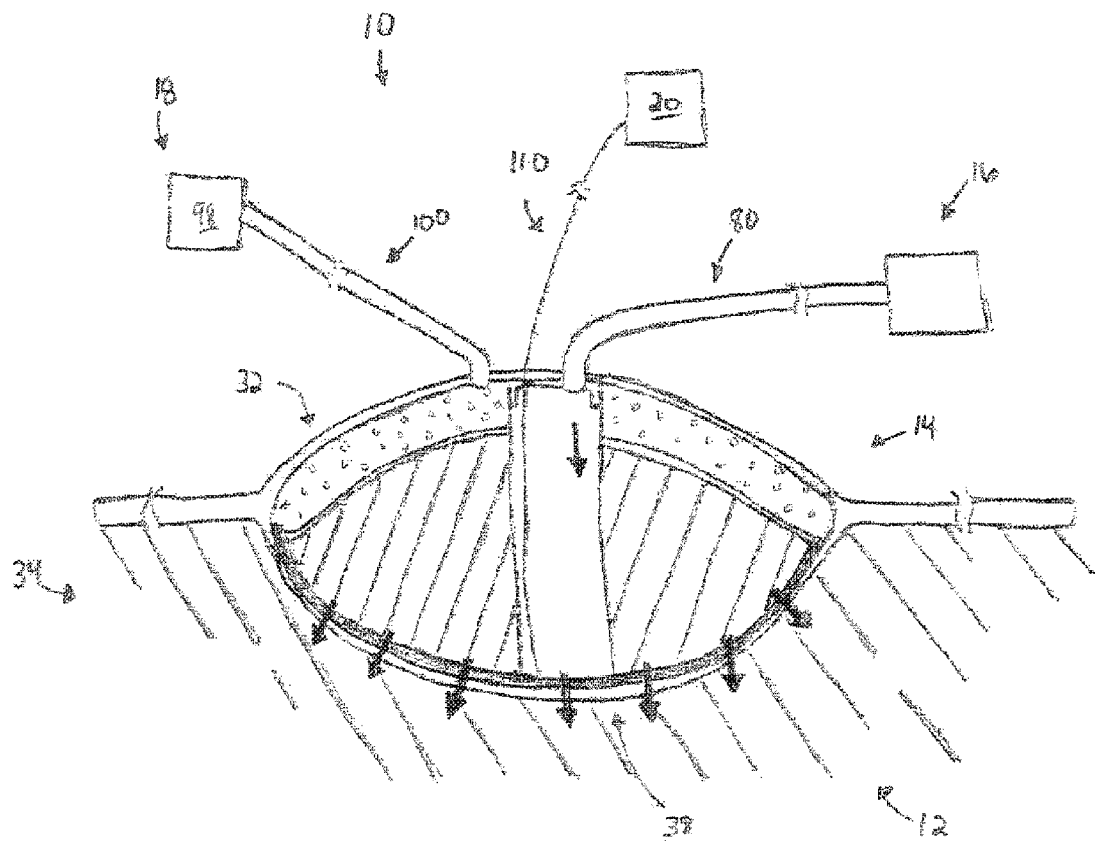
FIG. 8 is a cross-sectional view showing therapeutic agents being delivered into the wound in FIG. 7 (indicated by arrows)

Next, the power source 20 is activated so that at least one therapeutic agent comprising the solution is motivated into the wound 12 and/or the tissue surrounding the wound (FIG. 8). Activation of the power source 20 provides one or more electrical signals to the at least one electrode 54, which polarizes the at least one therapeutic agent and causes the polarized therapeutic agent to be motivated into the wound 12 and/or the tissue surrounding the wound via an electromotive force. The characteristics of the electrical signal(s) (e.g., frequency, voltage, etc.) can be varied as needed, as long as migration of the at least one therapeutic agent is aided by the electromotive force.

In one example of the present invention, the at least one therapeutic agent can be motivated into the wound 12 and/or the tissue surrounding the wound via iontophoresis. To deliver the at least one therapeutic agent via iontophoresis, the at least one electrode 54 of the system 10 can comprise a treatment electrode and a return electrode. Additionally, the power source 20 can include a low-voltage, DC or AC signal generator having positive and negative terminals (not shown) that are in electrical communication with the treatment electrode and the return electrode, respectively. Activation of the power source 20 will cause the treatment and return electrodes to obtain opposite charge polarities. The opposite charge polarities will then cause at least one therapeutic agent to ionize. The ionized therapeutic agent will then be driven into the wound 12 and/or the tissue surrounding the wound as result of the repulsive force between the treatment and return electrodes. Where the therapeutic agent comprises silver, for example, activation of the power source 20 can cause ionized silver ions to migrate into the bed sore(s) of the subject and thereby kill any bacteria present therein.

In another example of the present invention, the at least one therapeutic agent can be motivated into the wound 12 and/or the tissue surrounding the wound via dielectrophoresis. Dielectrophoresis involves providing a non-uniform AC or DC electric field to a compound or therapeutic agent. The non-uniform electric field, in addition to inducing a dipole in the compound or agent, sets up an electrical field gradient that provides an electromotive force on the newly polarized compound or agent, the magnitude and direction of which are dependent on several factors. A more detailed explanation of dielectrophoresis and its operating principles are disclosed in U.S. patent application Ser. No. 11/874,859 (hereinafter, "the '859 application") and Ser. No. 13/107,582, the entirety of each of which is hereby incorporated by reference.

To deliver the therapeutic agent via dielectrophoresis, the at least one electrode 54 of the system 10 can comprise an interdigitated electrode. In general, an interdigitated electrode can include any set of at least two electrodes that contain interwoven projections. For example, the interdigitated electrode can be comprised of a first electrically-conductive member that is separated by an insulator from a second electrically-conductive member. Each of the first and second electrically-conductive members can comprise a "comb" electrode (i.e., an electrode having a number of relatively long, flat prongs that are evenly spaced) whose prongs are interleaved with one another. The interdigitated electrode can additionally include at least one passage sufficient to allow at least one therapeutic agent to pass therethrough. More specific details concerning the design and function of interdigitated electrodes are disclosed in the '859 application.

The power source 20 can be activated to send an AC signal having certain characteristics to the interdigitated electrode. The power source 20 can be activated to cycle through at least one decade of frequencies ranging from about 0.1 Hz to about 20,000 Hz. For example, an AC signal can have an orienting frequency of about 0.1 Hz to about 100 Hz, a motivating frequency of between about 100 Hz and about 20,000 Hz, and an amplitude of between about 1 V to about 10 V. Additionally, an AC signal can be applied for between about 1 minute and about 30 minutes. A more specific description of the electrical signal and the logic used to modulate the electrical signal is disclosed in the '859 application.

Application of the electrical signal motivates at least one therapeutic agent into the wound 12 and/or the tissue surrounding the wound. For example, application of an AC signal to the interdigitated electrode provides a non-uniform electric field that induces a dipole on the at least one therapeutic agent. This, in turn, sets up an electrical field gradient that provides an electromotive force on the newly polarized therapeutic agent to drive the agent into the wound 12 and/or the tissue surrounding the wound.

Figure 9:
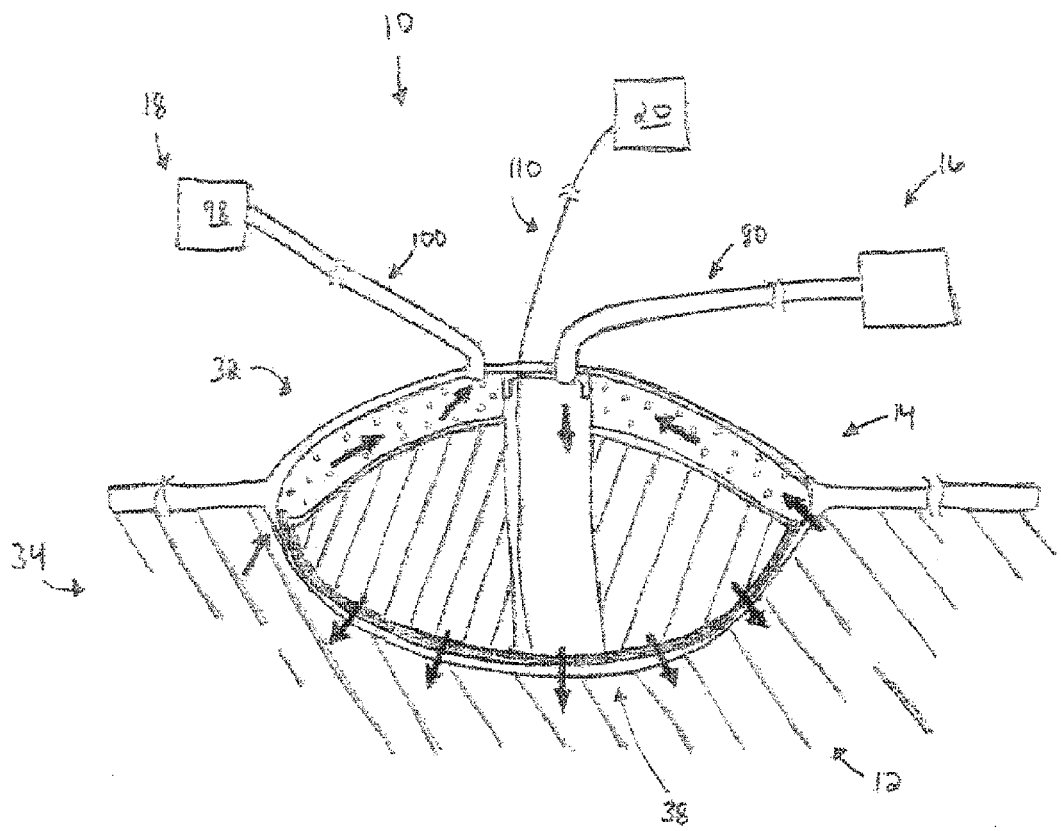
FIG. 9 is a cross-sectional view showing continuous delivery and removal of fluid and/or debris from the wound (indicated by arrows).

Either before, simultaneous with, or subsequent to delivery of the solution containing the therapeutic agent(s), the suction mechanism 18 is activated to suction fluid and/or debris from the wound 12 at Step 128. In particular, the vacuum source 98 is activated so that negative pressure or suction is created within the first porous material 48. As shown in FIG. 9, the negative pressure or suction causes fluid (e.g., solution containing the therapeutic agent(s), blood, puss, etc.) and/or debris (e.g., bacteria, fungi, scab fragments, cellular debris, etc.) to be pulled through the uptake ports 46, into the first porous material 48, and through the second fluid line 100 into a waste reservoir (not shown).

It is known that operation of conventional electromotive devices (e.g., iontophoresis and dielectrophoresis devices) can create unwanted localized pH alterations at the wound site due to accumulation of electrolysis products, cellular necrosis, and build-up of dead tissue. Such alterations can shield microorganisms, such as bacteria and fungi from delivery of the therapeutic agents and thereby contribute to further wound development. By removing unwanted fluid and/or debris during treatment, an optimal healing environment is created by the method 120. Additionally, continuous delivery of the solution containing the therapeutic agent(s) along with application of negative pressure or suction advantageously creates a flow pattern (collectively indicated by arrows in FIG. 9) about the wound 12 so that the therapeutic agent(s) can flow all over the wound bed. By manipulating the amount of negative pressure and the flow rate of the solution containing the therapeutic agent(s), the flow pattern created about the wound site can be selectively controlled for optimal tissue perfusion and treatment efficiency.

As indicated at Step 130 of the method 120, Steps 126 and 128 can be optionally repeated until the wound 12 is sufficiently healed.

From the above description of the invention, those skilled in the art will perceive improvements, changes and modifications. Such improvements, changes, and modifications are within the skill of the art and are intended to be covered by the appended claims.

Having described the invention, the following is claimed:

1. A method for healing a wound, said method comprising the steps of:
   (a) providing a system comprising a flexible body, a therapeutic agent delivery mechanism, a suction mechanism and a power source, the flexible body including a cover film having oppositely disposed first and second surfaces that define a compartment, the compartment including a first porous material, a second porous material, and at least one electrode disposed therein, the second porous material being disposed between the first porous material and the at least one electrode, the therapeutic agent delivery mechanism and the suction mechanism being in fluid communication with the compartment, the power source being in electrical communication with the at least one electrode, wherein a sheet member is disposed between said first and second porous materials, said sheet member preventing the movement of fluid between said first and second porous materials;
   (b) placing a wound-contacting portion of the compartment into contact with the wound;
   (c) delivering at least one therapeutic agent to the wound; and
   (d) activating the suction mechanism to remove at least one of fluid or debris from the wound;
   (e) optionally repeating steps (c)-(d) until the wound is sufficiently healed.

2. The method of claim 1, wherein steps (b)-(d) create a controlled flow pattern of the at least one therapeutic agent about the wound.

3. The method of claim 1, wherein said therapeutic agent delivery mechanism further comprises:
   a valve;
   a therapeutic agent source in fluid communication with said valve; and
   an oxygen source in fluid communication with said valve.

4. The method of claim 1, wherein said suction mechanism further comprises a vacuum source in fluid communication with the compartment.

5. The method of claim 3, wherein said step of delivering the at least one therapeutic agent to the wound further comprises the steps of:
   causing the at least one therapeutic agent and oxygen to flow through the valve into the compartment; and
   activating the power source so that the at least one therapeutic agent is motivated into the wound.

6. The method of claim 5, wherein the at least one therapeutic agent is motivated into the wound via iontophoresis.

7. The method of claim 5, wherein the at least one therapeutic agent is motivated into the wound via dielectrophoresis.

8. The method of claim 4, wherein said step of activating the suction mechanism to remove at least one of fluid or debris from the wound further comprises activating the vacuum source so that fluid and/or debris is suctioned through the wound-contacting portion of the compartment.

9. The method of claim 8, wherein activation of the vacuum source creates negative pressure or suction within the first porous material.

* * * * *